United States Patent [19]

Bergstrom et al.

[11] Patent Number: 5,332,570
[45] Date of Patent: Jul. 26, 1994

[54] REDUCING SOLUTION FOR PERMANENT WAVE

[75] Inventors: Joan M. Bergstrom, Minneapolis; James M. Wilmott, Plymouth, both of Minn.

[73] Assignee: Dowbrands Inc., Indianapolis, Ind.

[21] Appl. No.: 963,168

[22] Filed: Oct. 19, 1992

[51] Int. Cl.⁵ .................... A61K 7/09; A61K 7/11
[52] U.S. Cl. .................... 424/72; 424/71; 132/203
[58] Field of Search ............ 424/72, 71, 70; 132/203

[56] References Cited

U.S. PATENT DOCUMENTS 4,786,493  11/1988  Smith .................... 424/97

FOREIGN PATENT DOCUMENTS 085894  8/1983  European Pat. Off. ........ 424/72
261387  3/1988  European Pat. Off. .
136857  4/1982  Japan .
63-146808  6/1988  Japan .
7303852  9/1973  Netherlands .

*Primary Examiner*—Paul R. Michl
*Assistant Examiner*—Sally Gardner

[57] ABSTRACT

Disclosed is an improved reducing solution comprising: a) from about 1.0% to about 11.0% by weight of cysteamino hydrochloride; b) from about 1.0% to about 24% by weight of a reducing agent selected from a group consisting of salts and esters of thioglycolic acid, L-cysteine, thiolactic acid, and thiomaleic acid, dithioerythreitol, and dithiothyreitol; c) from about 0.5% to about 7% by weight of isoascorbic acid; d) a base in amounts sufficient to adjust the pH from about 6.5 to about 8.5; and e) water in amount sufficient to total 100 percent of the solution; the weight percents being based upon the total weight of the solution.

11 Claims, No Drawings

REDUCING SOLUTION FOR PERMANENT WAVE

This invention relates to an improved reducing solution for permanent waving of the hair.

BACKGROUND OF THE INVENTION

Permanent waving of the hair broadly involves two steps. The first step is the reducing step which involves an application of a reducing solution to hair to cleave S-S bonds of protein chains in the hair. The second step is the oxidation step which involves application of the oxidizing agent to restore the S-S-bonds in the new rearranged position. Wetting agents or other penetrants are normally employed to aid the reduction step. The efficiency of the reducing solution depends on pH, and the temperature employed, which may be up to about 60° C.

The reducing step is generally carried out under alkaline conditions. The rearrangement of the S-S bonds results from both the mechanical stress put on the hair by the mandrels or waving rods and from the action of the alkali. The alkali serves to swell the hair by allowing the dissociated sulfur atoms generated by the cleavage of S-S bonds, to slip past one another more easily under the stress applied by the rods.

Under acid conditions the wave forming capacity of the reducing solution is drastically reduced making it necessary to apply heat to achieve a proper hair restructure.

In the oxidation step, the disulfide bonds are reformed in their new "curled" formations by an oxidizing agent such as bromic acid salts, perboric acid, hydrogen peroxide and the like.

There is a continuing effort to enhance the penetration of the reducing solution on the hair and accelerate the reducing step.

WO 90/03780 discloses the use of a reducing agent containing cysteine or its derivatives or cysteamine in combination with a mercapto compound selected from mercapto-ethanol, thiomalic acid, thiolactic acid and alpha-mercaptoethane sulfonic acid. Japanese Patent Application No. 57-62217 discloses the use of a reducing solution containing cysteamine hydrochloride in combination with a conventional reducing agent at a pH of about 9.

The reducing solutions of the prior art are generally inadequate for the production of a satisfactory curl, the durability of the curl over time, or in the clinical safety of the reducing agents.

It would be desirable to develop a reducing solution which provides a faster, more efficient curl at comfortable temperatures with minimum hair damage.

SUMMARY OF THE INVENTION

It has been suprisingly discovered that addition of isoascorbic acid to a permanent wave solution comprising a mixture of cysteamine hydrochloride (cysteamine) and one of thio compounds described below provides not only an efficient curl but also a longer lasting curl at about 23° C. at a pH of about 6.5 to about 8.5.

The present invention relates to an aqueous reducing solution comprising: a) from about 1.0% to about 11.0% by weight of cysteamine hydrochloride; b) from about 1.0% to about 24% by weight of a thio compound selected from a group consisting of salts and esters of thioglycolic acid, L-cysteine, thiolactic acid, and thiomaleic acid, dithioerythreitol, and dithiothyreitol; c) from about 0.5% to about 7% by weight of isoascorbic acid; d) a base in amounts sufficient to adjust the pH from about 6.5 to about 8.5; and e) water in amount sufficient to total 100 percent of the solution; the weight percents being based upon the total weight of the solution.

DETAILED DESCRIPTION OF THE INVENTION

Broadly, the amount of cysteamine in the reducing solution ranges from about 1.0% to about 11.0% by weight of the total weight of the solution. Preferably, the weight percent ranges from about 5% to about 7% by weight of the solution. The most preferred weight percent of cysteamine is about 5% by weight of the solution.

The reducing solution of the invention further contains at least one thio compound selected from salts and esters of thioglycolic acid, L-cysteine, thiolactic acid, and thiomaleic acid; dithioerythreitol, and dithiothyreitol. The amount of the thio compound ranges from about 1.0% to about 24% by weight of the composition.

Broadly, the ratio of the weight percent of cysteamine to the thio compound generally ranges from about 10:90 to about 90:10, with the prefered ratio being 30:70 and 40:60, and the most preferred weight percent ratio being 40:60.

Monoethanolamine thioglycolate (MEATG) is the most preferred thio compound. In the most preferred embodiment, the ratio of the weight percent of cysteamine to that of MEATG is about 40:60 with weight percent of cysteamine being about 5% and that of MEATG (40% active) being about 12% of the weight of the reducing solution. The total amount of cysteamine and MEATG in the most preferred embodiment should yield about 1.08 milliequivalents of sulfhydryl reducing equivalents in the solution.

Broadly, the amount of Isoascorbic acid used ranges in amounts from about 0.5% to about 7% by weight of the waving solution. More preferred amount of isoascorbic acid is from about 1.5% to about 2% by weight of the solution with the most preferred amount being about 2%.

The pH of the reducing solution is adjusted by addition of a base which includes ammonium hydroxide, sodium hydroxide, potassium hydroxide, monoethanolamine, diethanolamine and triethanolamine in amounts sufficient to provide a pH in range from about 6.5 to about 8.5. Monoethanolamine is the most preferred base used. The most preferred pH is about 8.0.

The reducing solution may further contain a surfactant selected from anionic, nonionic or amphoteric surfactants may be used to make hair more hydrophilic and more easily penetrable by the aqueous permanent wave solution of the invention. Surfactant in an amount from about 0.5% to about 8% by weight of the solution is found to be useful. A preferred surfactant is Poloxamer 188.

Chelating agents in the amounts from about 0.5% to about 2% by weight of the solution have been found to be effective in reducing the odor of the solution. The chelating agent or chelator is selected from a group consisting of ethylenediaminetetracetic acid and its salts and derivatives, L-arginine, B-cyclodextrin, glycine, and organophosphonates. The most preferred chelator is trisodium salt of N-(hydroxyethyl)ethylenediaminetriacetic acid used in the amounts of about 2% by weight of the solution.

Other optional indgredients known in the art for personal care products such as fragrances, thickeners, opacifiers, and conditioning agents such as cationic polymers and the like may be added to obtain the desired properties.

Water is added in amounts sufficient to total 100% by weight of the solution. Preferably deionized water is used.

METHOD OF PREPARATION

The reducing solution of the invention is prepared by mixing together the essential and optional ingredients. If the surfactant used is solid, the surfactant is melted first, and the fragrance added to it before mixing the surfactant with a premix of the remaining ingredients. A base is then added to adjust the pH to the desired range.

EFFICIENCY MEASUREMENT

The permanent waving efficiency of the solution is measured by a peg board method similar to the methods known in the art. A predetermined length of the tresses is wound with even tension around the pegs arranged in a zig-zag pattern and treated with a permanent waving solution. After a period of exposure to the reducing waving soltion, the hair is rinsed and set with an oxidizer in a conventional manner. The wet hair is removed from the pegs and the length of a portion of the waved tress is compared with the length of a similar portion of the rows of the pegs. Efficiency is indicated as a percentage based on the increased length of the waved tress as compared with the distance between the respective pegs. An efficiency of 100% represents hair that did not change dimension upon removal from the pegs. Generally, an efficiency in the range of about 60% to about 85% is desired.

The following examples further illustrate the preferred embodiments within the scope of the present invention. The examples are given solely for the purposes of the illustration and are not construed as limitation of the present invention as many variations of the invention are possible without departing from its spirit and scope. The stated amounts are in weight percents unless indicated otherwise.

EXAMPLES

A series of studies were conducted to illustrate the improved efficiency, and improved durability of the curl obtained from the reducing solution of the invention.

WAVING EFFICIENCY

The efficiency was measured as follows:

About 0.5 grams of hair tresses, each tress being 20 cm long, are used for measuring the waving efficiency of the solution. About 14.7 cm are wound with even tension, between points A and B about 4 cms apart (about 6 wave lengths), around the pegs arranged in a zig-zag pattern on a wave board similar to the peg boards known in the art. Wrapped peg boards are submerged for approximately five seconds at room temperature (about 23° C.) in the permanent wave solution. The boards are then placed inside ZIPLOC* bags at room temperature for intervals of about 10, 20 and 30 minutes respectively. Each peg board is then rinsed thoroughly with warm water for about five minutes.

The peg boards are blotted, immersed in a 2% hydrogen peroxide solution for about five seconds, and left damp for five minutes. Each peg board is rinsed with warm water for about five minutes.

The peg boards are blotted, the tresses removed from the peg boards, and the "wet" lengths of the tresses measured and recorded.

The curl efficiency is calculated from the equation below:

$$\left(\left(1 - \frac{(x - 4)}{(14.7 - 4)}\right)\right) \times 100 = y$$

where x is the permed hair length (cm) between the two points A and B, and y is the perm efficiency (%).

The permed hair tress can attain a maximum curl of 4 cms resulting in 100% perm efficiency or the tress may measure 14.7 cm in length resulting in no curl and 0% perm efficiency.

Table I illustrates the waving efficiency at 23° C. for solutions within and without the scope of the invention as a function of time and pH. The solutions were prepared by mixing the stated amounts of various ingredients in the manner described above. The ratio of weight percent of MEATG to that of cysteamine is 60:40. MEATG used is 40% active.

TABLE 1

| Reducing Agent | Isoascorbic acid | Time Minutes | Curl Efficiency pH7 | % Curl Efficiency pH8 | Hair-Length pH7 | pH8 |
|---|---|---|---|---|---|---|
| MEATG/ | — | 10 | 54.2 | 65.4 | 8.9 | 7.7 |
| Cysteamine | | 20 | 57.9 | 65.4 | 8.5 | 7.7 |
| (60:40) | | 30 | 61.7 | 72.0 | 8.1 | 7.0 |
| MEATG/ | 2% | 10 | 56.1 | 62.6 | 8.7 | 8.0 |
| Cysteamine | | 20 | 64.3 | 72.9 | 7.8 | 6.9 |
| (60:40) | | 30 | 64.5 | 70.1 | 7.8 | 7.2 |

The results of Table 1 indicate that the solution containing MEATG, cysteamine and isoascorbic acid provides a curl with about 73% efficiency at pH 8 after 20 minutes at about 23° C. as compared to the solution containing a mixture of MEATG and cysteamine under the same conditions.

Durability of the curl obtained after 30-minute treatment with the reducing solutions within and without the scope of the invention was determined in the manner described below.

DURABILITY TEST METHOD

The durability of the curl is determined by shampooing the curled tresses. The tresses are held in a palm of the hand and about 1 milliliter of shampoo is placed in the palm holding the tress. A lather is built up by rubbing the tresses with the shampoo with the palm of the other hand, with both hands working in an opposite circular motion with respect to each other. The tresses are then rinsed in water at 100° C. for about 20 seconds and blotted. The length of the curled tress is then measured to determine the change in the curl. The shampoo, the rinse, and the measurement steps are repeated for five times and ten times to determine the duration of the curl after 5 and 10 shampoos respectively. Table 2 illustrates the results of the durability test. The lower the percentage changer the more durable is the curl.

TABLE 2

| Reducing Solution | Isoascorbic acid | | after 5 shampoos pH7 | pH8 | after 10 shampoos pH7 | pH8 |
|---|---|---|---|---|---|---|
| MEATG/Cysteamine (60:40) | | length (cm) | 10.0 | 9.3 | 10.0 | 9.4 |
| | | efficiency (%) | 43.9 | 50.5 | 43.9 | 49.5 |
| | | change (%) | 19.0 | 24.7 | 19.0 | 25.5 |
| MEATG/Cysteamine (60:40) | 2% | length (cm) | 8.9 | 8.5 | 9.2 | 8.9 |
| | | efficiency (%) | 54.2 | 57.9 | 51.1 | 54.2 |
| | | change (%) | 12.4 | 15.3 | 15.2 | 19.1 |

The results in Table 2 indicate that the percent change in the curl obtained from the solution of the invention containing MEATG, cysteamine and isoascorbic acid is lower both at pH 7 and pH 8 as compared to the curl obtained from the solution containing a mixture of MEATG and cysteamine. This result indicates that the curl obtained from the solution of the invention is more durable.

What is claimed is:

1. An aqueous reducing solution comprising: a) from about 1.0% to about 11.0% by weight of cysteamine hydrochloride; b) from about 1.0% to about 24% by weight of a thio compound selected from a group consisting of salts and esters of thioglycolic acid, L-cysteine, thiolactic acid, and thiomaleic acid, dithioerythreitol, and dithiothyreitol; c) from about 0.5% to about 7% by weight of isoascorbic acid; d) a base in amounts sufficient to adjust the pH from about 7.0 to about 8.0; and e) water in amount sufficient to total 100 percent of the solution; the weight percents being based upon the total weight of the solution.

2. The reducing solution of claim 1, wherein the thio compound is thioglycolic acid.

3. The reducing solution of claim 1, wherein the base is selected from the group consisting of ammonium hydroxide, monoethanolamine, triethanolamine, diethanolamine, potassium hydroxide and sodium hydroxide.

4. The reducing solution of claim 3, wherein the base in monoethanolamine.

5. The reducing solution of claim 4, wherein the pH is 8.0.

6. The reducing solution of claim 2 wherein the weight percent of cysteamine hydrochloride ranges from about 5 percent to about 7 percent by weight of the solution.

7. The reducing solution of claim 6 wherein the weight percent of cysteamine hydrochloride is about 5 percent by weight of the solution.

8. The reducing solution of claim 1, wherein the solution further comprises a surfactant selected from the group consisting of anionic, nonionic and amphoteric surfactants.

9. The reducing solution of claim 6, wherein the surfactant is Poloxamer 188.

10. The reducing solution of claim 1, wherein the solution further comprises a chelator selected from the group consisting of ethylenediaminetetracetic acid and, trisodium salt of N-Chydroxyethyl)ethylenediaminetriacetic acid, L-arginine, B-cyclodextrin, glycine, and organophosphonates.

11. The reducing solution of claim 10, wherein the chelator is trisodium salt of N-(hydroxyethyl)ethylenediaminetriacetic acid used in an amount of about 2 percent by weight of the solution.

* * * * *